United States Patent [19]

Saudek et al.

[11] Patent Number: 4,745,161

[45] Date of Patent: May 17, 1988

[54] SOLUBLE AND BIODEGRADABLE POLYAMINO ACID ACTIVATED FOR BONDING OF BIOLOGICALLY ACTIVE COMPOUND

[75] Inventors: Vladimír Saudek; Frantisek Rypacek; Jaroslav Drobnik, all of Prague, Czechoslovakia

[73] Assignee: Ceskoslovenska akademie ved, Czechoslovakia

[21] Appl. No.: 846,707

[22] Filed: Apr. 1, 1986

[30] Foreign Application Priority Data

Apr. 10, 1985 [CS] Czechoslovakia .................. 2634/85

[51] Int. Cl.[4] ............................................. C08G 69/48
[52] U.S. Cl. ................... 525/420; 528/310; 528/322; 528/328
[58] Field of Search .................. 525/420; 528/310, 328

[56] References Cited

U.S. PATENT DOCUMENTS 4,435,547 3/1984 Woo et al. ........................ 525/420

FOREIGN PATENT DOCUMENTS 17084 8/1964 Japan .
8590 1/1974 Japan .

OTHER PUBLICATIONS

Cols. 1–2, 35–36, U.S. Pat. No. 3,306,875, Hay.

Primary Examiner—Harold D. Anderson
Attorney, Agent, or Firm—Leydig, Voit & Mayer

[57] ABSTRACT

The invention pertains to copolymers activated for bonding of biologically active compounds and to a method for preparation thereof.

Soluble and biodegradable copolymers activated for bonding of biologically active compounds which have their main chain formed from units of aspartic acid or glutamic acid, or both, or also from units of other amino acids, according to the general formula I

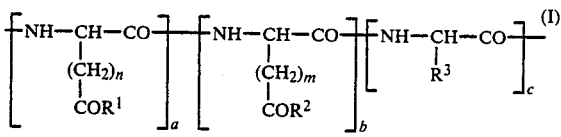

where n is 1 or 2, m is 1 or 2, a+b+c is 100, a is 0.5 to 100, b is 0 to 99.5, c is 0 to 80; the substituent $R^1$ is —NH—NH$_2$, —N≡N or

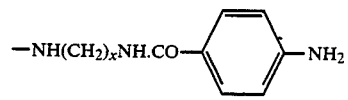

where x is 2 to 6, $R^2$ is —NH(CH$_2$)$_x$OH where x=2 to 6; and $R^3$ is methyl, 2-propyl, 2-methylpropyl, butyl, 2-butyl, benzyl or 4-hydroxybenzyl, and the molecular weight is 5,000 to 1,000,000.

2 Claims, No Drawings

SOLUBLE AND BIODEGRADABLE POLYAMINO ACID ACTIVATED FOR BONDING OF BIOLOGICALLY ACTIVE COMPOUND

BACKGROUND

The invention pertains to soluble and biodegradable copolymers which are activated for bonding of biologically active compounds.

Biologically active compounds bonded on soluble synthetic polymers have been proposed during recent years as suitable types of so called "prodrugs" for medical applications. Such bonded compounds enable, for example, longer excretion halftimes for active components, affects at active sites in the body, combining several activities, etc. Poly(aspartic acid) and poly(glutamic acid) and their derivatives are prospective polymers for such applications. Reactive functional groups must to be introduced into the polymers to bond chosen compounds. Poly(succinimide) is usually used for the synthesis, of poly(aspartic acid) as the reactive intermediate which is allowed to react with a reactive amine carrying a suitable functional group. However, this procedure always affords the racemic polymer which, moreover, contains both α and β peptide bonds in the main chain and, consequently, the resulting polymer is biodegradable with great difficulty.

The biodegradable derivatives of activated poly(aspartic acid) may be obtained by the polymerization of N-carboxyanhydrides of the β-monoester of the pertinent amino acid by deprotection of the carboxylic group through ester cleavage, and the subsequent activation of carboxylic group, e.g. with carbodiimide or formic esters. A disadvantage of this procedure is the complicated multistep synthesis, low yield, possible accumulation of undesirable side reactions, and incomplete conversion in the individual steps. In addition to this, polyanions with free carboxylic groups are not very suitable for practical medical application, and it is more convenient to prepare non-ionogenic derivatives with hydroxyl groups in the side chain. This requires, indeed, further reaction with aminoalcohols after bonding of a biologically active compound.

Preparation of poly(N-hydroxyethylglutamine) carrying 1-β-D-arabinofuranosylcytosine (ara-C) in the side chain may serve as an example of this procedure: Poly(γ-benzyl glutamate) was transferred to poly(glutamic acid) and ara-C and then aminoethanol were incorporated by means of isobutyrylcarbonyl chloride (Kato et al., Cancer Res. 44, 25 (1984)). The copolymer of glutamic acid and glutamic acid hydrazide was also prepared from poly(glutamic acid) by the reaction with tert-butyl carbazate by means of N-ethyloxycarbonyl-2-ethoxy-1,2-dihydroquinoline. The tert-butyl group was split off after reaction. This copolymer was employed for bonding of adriamycin by means of an acylhydrazone bond (Heeswijk et al., Rec. Adv. Drug Delivery Systems, Anderson Kim ed., Plenum Publishing Corporation, 1984, p. 77-100).

If the copolymer of hydroxyalkylglutamine and glutamic acid is prepared from polyalkylglutamate by an incomplete aminolysis of the ester groups followed by the hydrolysis, the carboxylic groups thus formed cannot be simply activated for the reaction with a biologically active compound without the parallel undesirable reaction between the hydroxyl groups of hydroxyalkylglutamine and carboxylic groups.

DISCLOSURE OF THE INVENTION

It has been found now that aminoalcohols catalyze the hydrazinolysis of esters so that it is possible to prepare copolymers of hydroxyalkylglutamines and hydroxyalkyl aspartagines with the corresponding hydrazides of monomeric units of glutamic and aspartic acids very easily by a single-step reaction. The starting material are polymeric esters, for example, poly(γ-benzyl glutamate) or poly(γ-methyl glutamate) or poly(β-alkyl aspartates), their mutual copolymers or copolymers with other amino acids, which are treated with a mixture of aminoalcohol and hydrazine. The ratio of these components in the reaction mixture controls the ratio of hydroxyalkylamide and hydrazide units in the resulting product. The reaction may be further accelerated by addition of 2-hydroxypyridine.

The copolymers with hydrazides of aspartic acid may also be prepared from poly(succinimide) or from copolymers of succinimide with other amino acids, again by the simultaneous reaction of aminoalcohol and hydrazine.

According to the invention, it is possible to bind compounds with aldehyde or ketone groups directly to the hydrazide-containing copolymers. Another way is the oxidation of hydrazide to azide which then easily reacts with both aromatic and aliphatic amines. The reaction may be carried out either in water or in organic solvents. The invention enables, in this way, the direct bonding of chosen compounds with an amino group, or the preparation of intermediates by bonding amines of the type

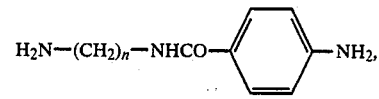

where n=0 to 6, which are then activated by diazotization.

The object of this invention is a soluble and biodegradable copolymer, activated for the bonding of biologically active compounds, wherein the main chain is formed from the units of aspartic acid or glutamic acid, or from both these units, or also from units of other amino acids, according to the general formula I

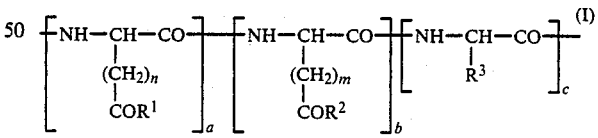

where n is 1 or 2, m is 1 or 2, a+b+c is 100, a is 0.5 to 100, b is 0 to 99.5, c is 0 to 80; the substituent $R^1$ is —NH—NH$_2$—, —N≡N or

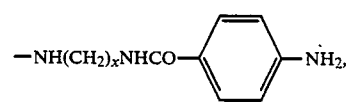

where x is 2 to 6; $R^2$ is —NH(CH$_2$)$_x$OH where x is 2 to 6; and $R^3$ is methyl, 2-propyl, 3-methylpropyl, butyl, 2-butyl, benzyl or 4-hydroxybenzyl, and the molecular weight is 5,000 to 1,000,000.

The object of this invention is further a method for preparation of the copolymer wherein a polymer having units of the general formula II

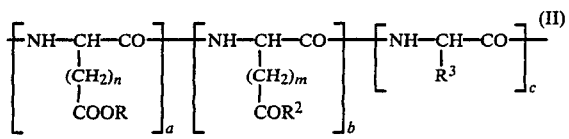

where R is methyl or benzyl, n is 1 or 2, m is 1 or 2, a+b+c is 100, a is 0.5 to 100, b is 0 to 99.5, c is 0 to 80, $R^2$ is R or is the same as in the general formula I, and $R^3$ is the same as in the general formula I, is treated at a temperature of from 0° C. to 60° C. with a mixture containing primary or secondary aminoalkylalcohol, wherein the alkyl is a linear or branched hydrocarbon chain having 2 to 6 carbon atoms, and hydrazine.

The object of the invention is also a method for the preparation of copolymers of aspartic acid, wherein poly(succinimide) reacts at temperature 0° C. to 60° C. with a mixture containing primary or secondary aminoalkylalcohol, wherein the alkyl is a linear or branched hydrocarbon chain having 2 to 6 carbon atoms, and hydrazine.

DESCRIPTION OF THE PREFERRED EMBODIMENTS

The invention is illustrated in the following examples, which, however, do not limit the scope of the invention by any means.

EXAMPLE 1

Poly(γ-benzyl L-glutamate) (2 g) was dissolved in 20 ml of dimethylacetamide and then a mixture of 86 μl of hydrazine and 1.5 ml of ethanolamine was dropwise added under vigorous stirring at ambient temperature. The stirring was continued for 20 min, the reaction mixture was then allowed to stand at 60° C. for 4 days, and then poured into 200 ml of ethanol containing 5 ml of acetic acid; the precipitate was separated by filtration, dissolved in the acidified water, dialyzed against water, and lyophilized. The product was 1.01 g of the copolymer of γ-hydrazide of L-glutamic acid (11 mol.%) and Nγ-(2-hydroxyethyl)-L-glutamine (89 mol.%).

EXAMPLE 2

Poly(succinimide) (2 g) was dissolved in 20 ml of dimethylformamide and a mixture of 144 μl of hydrazine and 2.5 ml of ethanolamine was dropwise added under stirring and cooling to 0° C. The reaction mixture was then stirred at ambient temperature overnight and worked out in the same way as in example 1. The product was 1.9 g of the copolymer of α,β-hydrazide of D,L-aspartic acid (12 mol.%) and $N^{\alpha,\beta}$-(2-hydroxyethyl)-D,L-aspartic acid (88 mol.%).

EXAMPLE 3

Poly(γ-benzyl L-glutamate) (1 g) was overcast with a mixture of 2.5 ml ethanolamine and 14 μl of hydrazine and allowed to stand at 60° C. for 4 days. The resulting solution was precipitated with 50 ml of ethanol containing 4 ml of acetic acid, the precipitate was washed with ethanol and ether and dried. The product was 0.77 g of the analogous copolymer as in example 1 which contained 1.3 mol.% of hydrazide.

EXAMPLE 4

The reaction was carried out in the same way as in example 1, but 2-hydroxybutylamine was used instead of ethanolamine. The product was 1.0 g of the copolymer of γ-hydrazide of L-glutamic acid (10 mol.%) and Nγ-(2-hydroxybutyl)-L-glutamine.

EXAMPLE 5

The reaction was carried out in the same way as in example 1, with the distinction that 3-hydroxybutylamine was used instead of ethanolamine. The product was 1.0 g of the copolymer of γ-hydrazide of L-glutamic acid (10 mol.%) and Nγ-(3-hydroxybutyl)-L-glutamine.

EXAMPLE 6

The copolymer of γ-benzyl L-glutamate with 3 mol.% of L-phenylalanine (1 g) was dissolved in 10 ml of dimethylacetamide and then 0.75 ml of the solution containing 3.1 mol.% of hydrazine; and 10 mol.% of hydroxypyridine in ethanolamine was dropwise added under vigorous stirring at ambient temperature. The preparation was continued as in example 1. The product was the terpolymer of γ-hydrazide of glutamic acid (9.6 mol.%), phenylalanine (3 mol.%) and Nγ-(2-hydroxyethyl)-L-glutamine.

EXAMPLE 7

The reaction was carried out in the same way as in example 6, with the distinction that the copolymer of γ-benzyl L-glutamate with 6 mol.% of leucine and the solution containing 2.5 mol.% of hydrazine in ethanolamine were used. The product was 0.48 g of the copolymer of γ-hydrazide of glutamic acid (8.4 mol.%), leucine (6 mol.%) and Nγ-(2-hydroxyethyl)-L-glutamine.

EXAMPLE 8

The reaction was carried out in the same way as in example 6, with the distinction that the copolymer of γ-benzyl L-glutamate with 4 mol.% of valine and the solution of 1.9 mol.% hydrazine in ethanolamine were used. The product was 0.51 g of the terpolymer of γ-hydrazide of glutamic acid (6.6 mol.%), valine (4 mol.%) and Nγ-(2-hydroxyethyl)-L-glutamine.

EXAMPLE 9

The polymer resulting in example 1 was dissolved in 3 ml of 0.1 mol/l HCl and 1 ml of 0.1 mol/l sodium nitrite (NaNO₂) and, after 5 min, the suspension of 39 mg of N-(6-aminohexyl)-2,4-dinitroanilide (AHDN) dihydrochloride in 20 ml of 0.2 mol/l sodium hydrogencarbonate (NaHCO₃) were successively added under stirring and cooling to 0° C. After 2 hours of stirring, the solution was transferred into a dialysis tube, dialyzed against water and freeze-dried. The resulting preparation contains N-(6-aminohexyl)-2,4-dinitroanilide (AHDN) bonded to 11 mol.% of monomer units.

EXAMPLE 10

To the solution of 100 mg of the polymer prepared in example 2 in 2 ml of dimethylsulfoxide (DMSO) it was successively added under stirring and cooling to 0° C. 1 ml of 0.1 mol/l hydrochloric acid (HCl) in methanol, a mixture of 0.5 ml of butyl nitrite and 4.5 ml of dimethylsulfoxide (DMSO) and, after 5 min, a solution of 0.139 ml of triethylamine and 39 mg of N-(6-aminohexyl)-2,4-dinitroanilide (AHDN) dihydrochloride in 10 ml of dimethylsulfoxide (DMSO). After 2 h, the reaction mixture was dialyzed against water and freeze-dried. The resulting preparation contained N-(6-aminohexyl)-2,4-dinitroanilide bonded to 11% of monomer units.

EXAMPLE 11

45 mg of the polymer prepared in example 6 was disolved in 10 ml of 0.1 mol/l hydrochloric acid and cooled to 0° C. Under stirring and cooling 10 ml of 0.1 mol/l sodium nitrite was added to it followed, after 5 min by a solution of 10 mg of adriamycin in 0.1 ml of methanol and 10 ml of 0.1 mol/l sodium hydrogenphosphate. After 2 h, the resulting solution was applied on a column with Sephadex G-26 and the separated high-molecular-mass fraction was lyophilized. The resulting preparation contained adriamycin bonded to 9.6% of monomer units.

EXAMPLE 12

50 mg of the polymer prepared in example 2 was disolved in 10 ml of 0.1 mol/l hydrochloric acid and cooled to 0° C. Under stirring and cooling 10 ml of 0.1 mol/l sodium nitrite ($NaNO_2$) was added to it followed, after 5 min by a solution of 40 mg cytosine in 10 ml of 0.1 mol/l sodium hydrogencarbonate ($NaHCO_3$). After 2 h, the high-molecular-mass fraction was separated by gel filtration through Sephadex G-26. The resulting preparation contained cytosine bonded to 0.5% of monomer units.

EXAMPLE 13

The reaction was carried out in the same way as in example 11, with the distinction that 38 mg of cytosine-β-D-arabinofuranoside hydrochloride (ara-C) was used. The resulting preparation contained ara-C bonded to 0.6% monomer units.

EXAMPLE 14

The reaction was carried out in the same way as in example 11, with the distinction that 40 mg of 5-aza-2'-deoxycytidine (Aza-C) was used instead of adriamycin. The resulting preparation contained Aza-C bonded to 0.6% of monomer units.

EXAMPLE 15

The reaction was carried out in the same way as in example 9, with the distinction that a solution containing 30 mg of 4-amino-N-(2-aminoethyl)benzamide hydrochloride (AABH) was used instead of N-(6-aminohexyl)-2,4-dinitroanilide. The resulting polymer contained 4-amino-N-(2-aminoethyl)benzamide hydrochloride (AABH) bonded to 11% of monomer units.

EXAMPLE 16

50 mg of the polymer prepared in example 15 was dissolved in 2.5 ml of 0.5 mol/l hydrochloric acid (HCl) and cooled to 0° C. Under stirring and cooling 0.25 ml of 1 mol/l sodium nitrite ($NaNO_2$) was added to it followed, after 5 min by 1 ml of 2 mol/l sodium carbonate ($Na_2CO_3$) and 0.26 ml of 1 mol/l sodium hydrogensulfite, and, after another 5 min, 9 mg of pancreatic trypsin and kallikrein inhibitor (TKI, specific antitryptic activity 4.2 BAPA U/mg) in 1 ml water. The non-bonded trypsin and kallikrein (TKI) were separated from the high-molecular-mass fraction by gel filtration through Sephadex G-50. The resulting high-molecular-mass preparation contained 17 weight-% trypsin and kallikrein inhibitor (TKI) and exhibited 0.15 antitryptic BAPA U/mg.

EXAMPLE 17

Adriamycin (10 mg) in 0.4 ml of methanol was added to the solution of 45 mg of the polymer prepared in example 1 in 10 ml of 0.1 mol/l acetate buffer with pH 5.05. After 7 days, the high-molecular-mass fraction was separated by gel filtration through Sephadex G-25 and freeze-dried. The resulting preparation contained adriamycin bonded to 11% of monomer units.

What is claimed is:

1. A biodegradable copolymer activated for bonding of biologically active compounds, wherein the main chain of the copolymer is formed from the units of aspartic acid or glutamic acid, or from both these units, or also from units of other amino acids, according to the general formula I

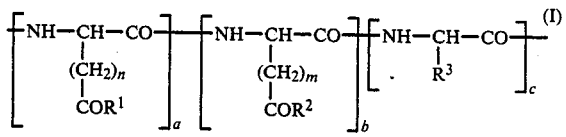

where n is 1 or 2, m is 1 or 2, a+b+c is 100, a is 0.5 to 100, b is 0 to 99.5, c is 0 to 80, substituent $R^1$ is —NH—$NH_2$, —N≡N or

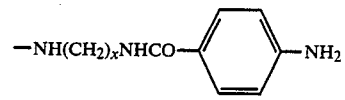

where x is 2 to 6; $R^2$ is —NH$(CH_2)_x$OH where x is 2 to 6; and $R^3$ is methyl, 2-propyl, 2-methylpropyl, butyl, 2-butyl, benzyl or 4-hydroxybenzyl.

2. Method for preparation of the copolymer according to claim 1, wherein a polymer having units of the general formula II

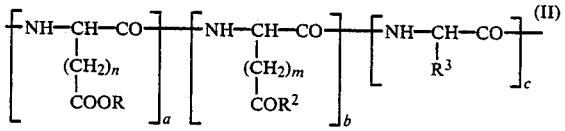

where R is methyl or benzyl, n is 1 or 2, m is 1 or 2, a+b+c is 100, a is 0.5 to 100, b is 0 to 99.5, c is 0 to 80; $R^2$ is R or is the same as in claim 1; and $R^3$ is the same as in the general formula I; is treated at 0° C. to 60° C. with a mixture containing primary or secondary amino alkylalcohol, wherein the alkyl is a linear or branched hydrocarbon chain having 2 to 6 carbon atoms, and hydrazine.

* * * * *